United States Patent [19]
Ruffini

[11] Patent Number: 4,655,755
[45] Date of Patent: Apr. 7, 1987

[54] EXTERNAL CATHETER

[76] Inventor: Lillian Ruffini, 210 Harmony Rd., West Grove, Pa. 19390

[21] Appl. No.: 790,098

[22] Filed: Oct., 1985

Related U.S. Application Data

[63] Continuation-in-part of Ser. No. 618,913, Jun. 8, 1984, abandoned.

[51] Int. Cl.⁴ .............................................. A61F 5/44
[52] U.S. Cl. .................................................... 604/352
[58] Field of Search ................................. 604/346–353

[56] References Cited

U.S. PATENT DOCUMENTS 2,586,674  2/1952  Lonne ................................. 604/349
2,864,369  12/1958  Morrow .............................. 604/353
4,239,044  12/1980  Paulinch ............................. 604/352

Primary Examiner—C. Fred Rosenbaum
Assistant Examiner—J. L. Kruter
Attorney, Agent, or Firm—Connolly and Hutz

[57] ABSTRACT

A catheter for males having an inner and outer sheath in which a helically wound airtight tube formed on the flexible inner sheath provides an expandible and contractible compartment adapted to accommodate changes in an engaged penis.

2 Claims, 6 Drawing Figures

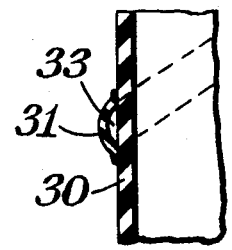
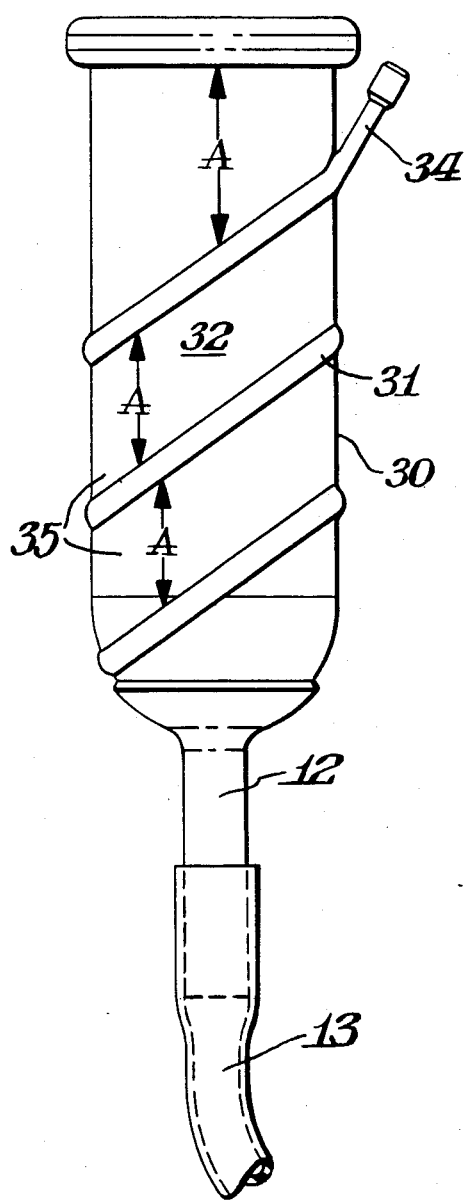
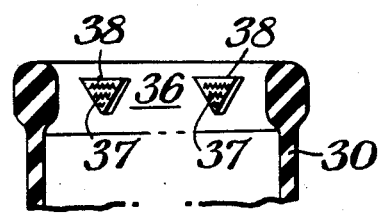

EXTERNAL CATHETER

This application is a continuation-in-part of copending application Ser. No. 618,913, filed June 8, 1984 now abandoned entitled External Catheter by Lillian Ruffini.

This invention relates to a member encircling therapeutic device and more particularly to a combination of cooperating elements utilized to make up a device for securing by a pneumatic force a condom type male catheter to the penis of a person suffering from a disorder requiring maintenance of means for draining urine.

BACKGROUND OF THE INVENTION

A disorder of incontinence requires a means for constantly draining and conducting urine to a receptacle. In males one type of device is an elastic external condom catheter which externally fits over and tightly clasps the penis and is found at the end of an integral tube. By various suitable means this tube portion is attached to tubing which interconnects the catheter to a receptacle.

The external male urinary catheter has the disadvantage that it is secured to the wearer by wrapping an adhesive strip around the penile shaft sufficiently tightly to ensure a grasp of the shaft that will maintain the catheter in place for an extended period of wear. If the desired effect is to be maintained the fastening must at the same time be able to accomodate changes in condition of the penile shaft and be comfortable. There are serious disadvantageous side effects of chafing and irritating the skin of the patient, if the adhesive strip is tightly wound, and loosens and disconnection if it is not sufficiently tight.

Previous attempts to solve these problems have not eliminated serious difficulties or objectionable situations. Two of these are stasis of urine and strangulation. Stasis of urine occurs, for example, when the head of the sheath collapses. It can occur when the retention pressure is applied only in one area, such as by a collar, or whenever retention is sought by a strap effect.

Strangulation occurs when the grip or retention is provided by a tight encircling of the penis in an effort to overcome the slippage which can occur on retraction of the penis.

The following identifies prior disclosures which involve previous efforts to provide means for drawing urine within external sheath.

In Pavlinch, U.S. Pat. No. 4,239,044 air is inserted by a bulb syringe. The user is unable to feel the resistance and document the current of air inserted—the air duct and valve of the present claim is more accurate. A set amount of air can be determined for each individual patient not, however, by a bulb syringe. In F. E. Koch, U.S. Pat. No. 2,699,781 a bulb used which cannot measure the air inserted for each individual and thus creates a continuous tight grip on penis. Urine in the bag will add more pressure to the penis. In R. B. Carrrigan, U.S. Pat. No. 3,535,241 there is complicated construction which when the penis retracts will possibly wet the scrotal area and cause regression or damage to the skin integrity in the area. Again, bulb type injection of air issued and no measurement means is noted. In Lawrence, U.S. Pat. No. 1,228,452 the structure presents a danger of stasis of urine. Other prior disclosures rely upon a strap-effect to secure the device in place. Thus they create the very problem the present invention overcomes.

It is an object of the present invention to enable the use of an external male catheter over an extended period of time during which the catheter remains in place under varying conditions during use and while avoiding irritation, discomfort, disengagement or leakage.

The present invention permits the construction and application of an external male urinary catheter of secure, permanent fit and attachment with a minimum of discomfort to the wearer and which is easy and simple in attachment and use.

SUMMARY OF THE INVENTION

A flexible, elastic compartment containing pneumatic pressure is formed in a unitary structure of a tubular configuration by an inner sheath and an outer tube curving around the outside of the sheath, the sheath and the tube being joined at airtight joints. The inner sheath has an interior adapted to receive a penis through an axial entrance and an interior surface engageable with the penis. The other end of the unitary catheter structure is formed to be adapted for drainage, as to a drainage tube to provide release of fluid from the catheter.

The tube-like channel around the inner sheath surrounds the inner sheath, and being joined to it by airtight joints. The outer tube has a stem or duct formed with a passage to provide for introduction of air under pressure into the compartment formed by the tube on inner sheath. The stem has a valve mechanism in the passage such as a check valve providing a one-way inlet path normally precluding egress of air, which permits introduction of air under pressure into the compartment but blocks its excape.

The outer tube curves around the outer surface of the inner sheath as a spiral or a helix. A helix follows the surface so as to become a straight line if the surface were unrolled in a plane. A spiral is a helix on a surface which is in one plane.

BRIEF DESCRIPTION OF THE DRAWINGS

For a complete understanding of the present invention reference can be made to the following description and to the accompanying drawings in which:

FIG. 4 is a perspective view of the device of the present invention, namely, an external male urinary catheter and a helix tubing;

FIG. 5 is a view of part of the wall of the catheter structure of FIG. 4 with a part of the tubing and sheath well shown in section; and FIG. 6 is a broken away part of the upper end of the sheath of FIG. 4 in section to show the interior.

DETAILED DESCRIPTION

Figure 1:
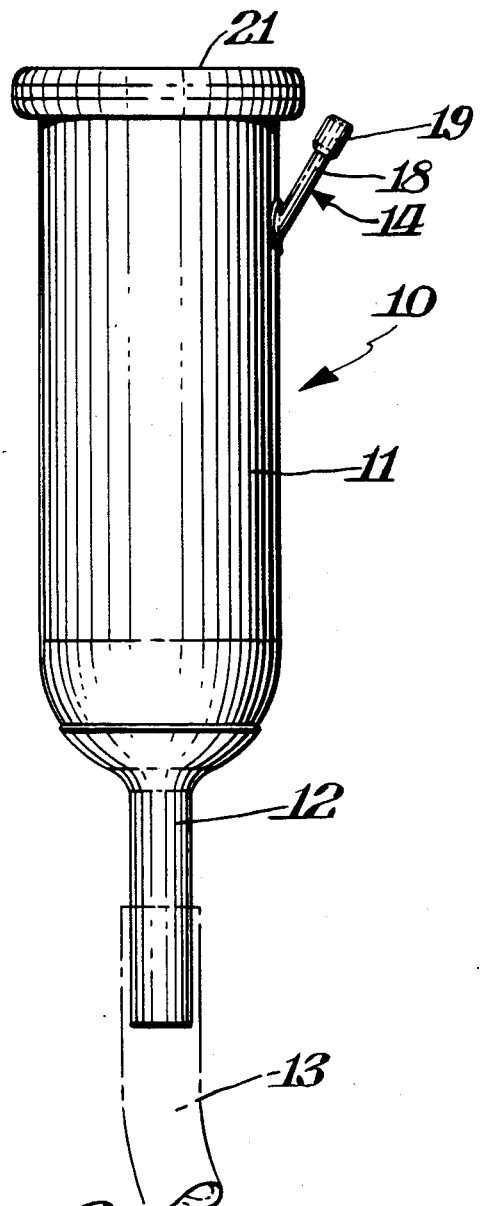
FIG. 1 is a perspective view of the device of the present invention, namely, an external male urinary catheter and attached tubing and means for introducing air under pressure into a sealed compartment within the catheter structure.

FIG. 1 shows an external catheter structure 10 in which an outer sheath structure 11 terminates in a conventional terminal tube 12 for attachment to drainage tube 13. The outer sheath 11 has a stem 14 attached to its exterior surface to provide a duct into the sheath.

The sheath 11, tube 12 and stem 14 are shown from below in FIG. 2.

Figure 2:
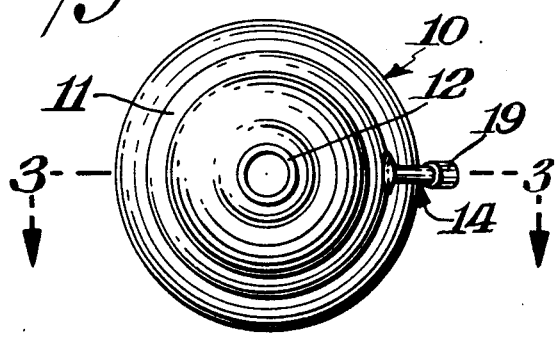
FIG. 2 is an end view of the catheter structure as seen from below FIG. 1.
Figure 3:
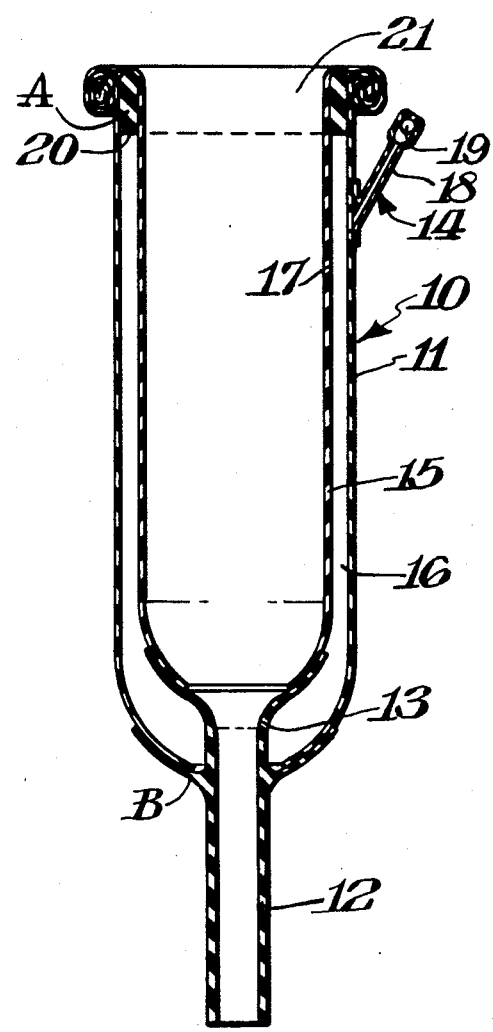
FIG. 3 is an axial section taken on line 3—3 of FIG. 2 of the catheter of this invention in inflated condition to show the compartment under pneumatic pressure.

FIG. 3 is an axial section of the unitary catheter structure taken on line 3—3 of FIG. 2. The sheath 11 is joined to an inner sheath 15 to enclose a compartment 16. As the joints between sheaths 11 and 15 are air tight compartment 16 can contain pneumatic pressure and is radially expandable and contractible with accompanying changes in pressure. The sheaths 11 and 15 are made of suitable elastic film, such as latex rubber. The sheath 15 has an interior surface 17 which is engageable with a penis and is designed to receive and expand around the penis of the wearer and to cling thereto securely. The outer sheath 11 of slightly greater diameter provides the compartment between sheaths 11 and 15. The catheter 10 is made up so that the sheath 15 and an outer sheath 11 are sealed together at airtight joints A and B to form and encompass the airtight compartment 16. The valve stem 14 provides ingress to the compartment 16 comprising a duct 18 extending laterally from sheath 11 and a ball and seat check valve 19. The terminal 12 and valve stem 14 are integral elements of the sheath 11.

As the sheaths 11 and 15 consists of flexible, elastic film material the compartment 16 is radially expandable and contractible to secure the engageability of the interior surface 17 on a wearer. Accordingly, the pneumatic pressure in the compartment 16 aids in the ability of the interior surface to cling when in use. Under the pneumatic pressure the interior surface bears evenly in its engagement and expansion or contraction of the engaged penis is matched with an accompanying reduction or enlargement of the compartment. The air is forced into the compartment under pressure and the check valve 19 precludes egress of air so that the duct 18 is normally a one-way inlet path.

When the structure 10 is in place in use a seal is formed between the interior surface 17 and the engaged penis which prevents escape of urine without the need for other sealing means.

The catheter 10 has a collar 20 of stiffer material adjacent the open end 21 of the tubular catheter 10, the sealing together of the sheaths 11 and 15 at B is in the area of the collar and the open end 21.

There may be provided a separate means for depressurizing (not shown) or the check valve may be designed to be adjustable to provide a release of pressure.

FIG. 4 shows a structure having an inner sheath 30 which is engageable with a penis and is designed to be worn by a user. A helical tubing 31 encircles an outer surface 32 of the sheath. The tubing 31 is sealed to the outer surface 32 to provide an airtight compartment 33 shown in FIG. 5. A valve stem 34 provides ingress to the compartment 33 and can be provided with a check valve, not shown. Pneumatic pressure is applied to compartment 33 which curves in the helix around the sheath 30.

The pneumatic pressure is thus applied at the places where the tubing 31 overlies the surface 32 and thus applies pressure at those limited but distributed areas of contact with the user. It is a feature that the successive curves of the tubing 31 are both integral with the sheath 30 and are spaced apart on the surface 32 by dimensions A on the sheath 30.

This arrangement of the encirclement by tubing 31 and the area of spacing 35 result in a distribution of pressure and gripping which serves to retain the sheath on a user and avoid both stasis and strangulation.

FIG. 6 illustrates the inner surface 36 of the upper end of the sheath 30. V-shaped protrusions 37 are raised slightly on the surface 36 adjacent the upper end and pointing toward the other end of the sheath 30. The protrusions 37 are formed on their inwardly facing surfaces with irregularities or scorings 38 to enhance the grip on the user. The protrusions 37 at the upper end are spaced from a curve of the tubing 31 also by a dimension A. The shape and position of protrusions 37 cooperate with the pressure at the tubing 31 to retain the sheath 30 on the user in different conditions of the user during use.

The advantages of the above-described invention overcome the deficiencies in the systems of drainage. Among the shortcomings that are substantially avoided is the detachment of the devce resulting in an undesirable situation. Also the attachment by pneumatic pressure permits a more secure yet less bothersome grasp of the device in place.

Other advantages of the pneumatic pressure applying external catheter are that mobility of the wearer is increased without the problem of slipping off. Further the close fit of the condom structure on the penile shaft reduces stasis of urine.

I claim:

1. A unitary penile catheter of a annular tubular form comprised of inner and outer sheaths and a air supply stem, said outer sheath and inner sheath having a coaxial tube means for attachment to a drainage tube, said inner sheath formed of a flexible elastic material and forming an expandable and contractible annular airtight compartment when air is supplied and removed from said compartment, said inner sheath having an inside and outside surface, said outside surface of said inner sheath having a helically wound airtight tubing sealed thereto along its length in which said tubing and inner sheath have an engagement area that maintains an even pressure of the inner sheath along its length on the penis, said air supply stem means providing a duct to provide air in said air tight helical tubing, whereby changes in the size of the engaged penis is accommodated by radial enlargement of the inner sheath or reduction size of the penis by collapsing of said inner sheath.

2. The structure as claimed in claim 1, wherein a plurality of V-shaped protrusions on the inner surface of said sheath adjacent an open end are positioned to cooperate with said engagement areas in engagement in use.

* * * * *